United States Patent [19]

Porubcan

[11] Patent Number: 4,681,759
[45] Date of Patent: Jul. 21, 1987

[54] RIOPROSTIL-PVP COMPLEX

[75] Inventor: Linda S. Porubcan, Readington, N.J.

[73] Assignee: Ortho Pharmaceutical Corporation, Raritan, N.J.

[21] Appl. No.: 731,701

[22] Filed: May 8, 1985

[51] Int. Cl.$^4$ .................. C07C 127/00; A61K 31/557; A61K 31/79

[52] U.S. Cl. ........................................ 424/80; 514/690

[58] Field of Search ............................ 424/80; 514/690

[56] References Cited

U.S. PATENT DOCUMENTS 3,826,823  7/1974  Orouke .................................. 424/80
4,301,146  11/1981  Sanvordeker ........................ 424/80

FOREIGN PATENT DOCUMENTS 3304867  8/1984  Fed. Rep. of Germany ........ 424/80

OTHER PUBLICATIONS

Fung et al., J. Pharm. Sci. 67, 971 (1978).
N. F. XV pp. 647 & 368 (III supp.) 1981.

Primary Examiner—Robert Gerstl

[57] ABSTRACT

A rioprostil/PVP complex is disclosed which is formed by lyophilization, evaporation or spray drying processes, and formed into improved solid dosage form for oral administration of cytoprotection and gastrointestinal lesions.

5 Claims, No Drawings

RIOPROSTIL-PVP COMPLEX

BACKGROUND OF THE INVENTION

1. Field of the Invention

This invention relates to a new molecular structure which is a complex of the known prostaglandin PGE, derivative, rioprostil, and polyvinylpyrrolidone (PVP) which is particularly useful as an improved dosage form for tablets and capsules.

Rioprostil is the United States Adapted Name (USAN generic name) for the compound which has also been referred to by the following names and code numbers:
(1) 1,11,16-trihydroxy-16-methyl-,(11α,13E)-prost-13-en-9-one; (2) (2R,3R,4R)-4-Hydroxy-2-(7-hydroxyheptyl)-3-[(E)-(4RS)-4-hydroxy-4-methyl-1-octenyl)]cyclopentanone; (3) CAS-77287-05-9; (4) TR-4698; (5) ORF-15927

Rioprostil exists, as do most prostaglandins, as an oil at room temperature. This oil is particularly viscous and was found on occasion to cause irritation to mucous membranes during routine handling. Both of these factors contribute to making rioprostil uncommonly difficult to handle. In addition, rioprostil was determined to have poor aqueous solubility and to be heat labile at room temperature. Rioprostil is a very potent medicinal substance and therefore requires a very low dosage strength. This posed a problem in that extreme manufacturing procedures would be required to insure content uniformity of the viscous oil from dose to dose in the desired tablet or capsule product. The instant invention solved these problems.

2. Description of The Prior Art

Rioprostil and its method of preparation are disclosed in U.S. Pat. No. 4,132,738 and U.S. Pat. No. 4,370,348. The latter patent teaches the use of rioprostil in a method of inducing cytoprotection in mammals, in a method of preventing gastrointestinal lesions, and, in a method of treating gastrointestinal lesions in mammals. The dosage level of rioprostil to be used in such disclosed methods of treatment is 2-200 micrograms, and the rioprostil may be administered in oral dosage form as a powder, capsule or tablet, using a pharmaceutical carrier such as starches, sugars, diluents, granulating agents, lubricating binders, disintegrating agents and the like. No specific carriers are disclosed and it has proved difficult to find good pharmaceutical carriers.

Efforts to find a good carrier for rioprostil are disclosed in three recently published German patent applications assigned to BAYER A G, namely; No. DE 3304-864-A teaches a stable adsorbate of rioprostil on dextran; No. DE 3304-880-A teaches a stable adsorbate of rioprostil on pregelatinized starch; and No. DE 3304-867-A teaches a stable adsorbate of rioprostil on crospovidone, which is a cross-linked polyvinylpyrrolidone.

BAYER patent application No. DE 3304-867-A states:

"The present invention furthermore relates to a process for the preparation of stable prostaglandin formulations in which the prostaglandin is applied in dissolved form to crosspovidone and is then dried. The present invention moreover relates to medicaments containing prostaglandins adsorbed onto crosspovidone and to the use of prostaglandins, or derivatives thereof, adsorbed onto crosspovidone in or as medicaments and for combating diseases, in particular for combating gastrointestinal ulcers, hypertension, bronchial asthma and thromboses, and for inducing labor and/or abortions in mammals.

In the context of the present invention, crosspovidones are understood as meaning polyvinylpyrrolidone crosslinked by further polymerization, especially a water-insoluble polyvinylpyrrolidone of this type. In the context of the present invention, crosspovidones which meet the specification of NF XV (National Formulary, 15 Edition, Official Nov. 1, 1981, the United States Pharmacoperial Convention, Inc.) are preferred."

The rioprostil crospovidone is a different material than the rioprostil/PVP complex of the present invention, which utilizes a non-cross-linked PVP, and also exists not as a mere physical mixture, but as a complex held together by chemical bonds with its own unique physical/chemical properties. Note that the cross-linked PVP referred to above is relatively insoluble in water, while the PVP used in the present invention is relatively soluble in water.

While PVP has often been used as the carrier for various prostaglandins, it has not been known in the form of a prostaglandin-PVP complex, as in the present invention.

SUMMARY OF THE INVENTION

The instant invention is a dry, solid form of a rioprostil: polyvinylpyrrolidone complex in the approximate proportions of 1 mole fraction rioprostil per $2\frac{1}{2}$ mole fraction of PVP monomeric subunits; said complex exhibiting, in comparison to uncomplexed rioprostil alone, increased solubility in water, improved stability in ethanol, and substantially improved thermal stability. Preferably, said complex will be ground to be in the form of a dry, yellow to white powder.

The instant invention also involves oral pharmaceutical preparations, e.g., tablets and capsules made from the above rioprostil/PVP complex.

DETAILED DESCRIPTION OF THE INVENTION

It has now been found that when rioprostil was combined with polyvinylpyrrolidone in the solution phase, properties were obtained unlike those of the original rioprostil and superior to rioprostil in many important pharmaceutical characteristics. Solubility in water, at ambient room temperatures, is increased from 800 µg/ml to 1160 µg/ml or an increase of 45% with the addition of 2% PVP in solution. Solution stability in ethanol is improved fourfold; the first order degradation rate decreased from $3.6 \times 10^{-3}$ hr$^{-1}$ to $0.866 \times 10^{-3}$ hr$^{-1}$ at 60° C. with the addition of 0.5% PVP in solution. It was also found that when the solvent was removed either by evaporative or freeze drying techniques, the resultant material existed as a yellow to white powder rather than an oily liquid. This facilitated the handling of the material and also decreased the potential for chemical irritation caused by the oil. The existence of the material as a solid made it easier to incorporate the drug into the dosage form. The rioprostil/PVP product can be accurately weighed for formulation with other tableting excipients, thereby assuring appropriate dosing. The powder can also be more easily blended with the excipients, so as to insure content uniformity in the total mix. In addition to these improved formulating factors, a preparation of 5% rioprostil in the PVP matrix afforded an unexpected improvement in the thermal stability of the drug in the solid state. When prepared by either evaporative or freeze drying techniques, rioprostil was about 40 times more stable than neat rioprostil drug substance at 80° C. over 22 days.

The rioprostil/PVP matrix obtained as stated above was further investigated because of the surprising change in both its solution solubility and stability, and particularly because of the dramatic improvement in solid state thermal stability. Complex formation between rioprostil and PVP was determined to be the explanation since (1) the equilibrium formation of a new species (complex) has properties different from those of the initial interactants and would explain the above changes in rioprostil physical/chemical properties, and (2) PVP is known to form complexes with other organic substrates (but not with prostaglandins). Complex formation in solution is the equilibrium reaction between substrate (rioprostil) and ligand (PVP) having the equilibrium:

$$mS + nL \rightleftharpoons SmLn$$

where m and n are integers describing the stoichiometry of the reaction. The complexation constant, $K_{mn}$, is defined as $$K_{mn} = \frac{[SmLn]}{[S]^m[L]^n}$$

Although a complex is defined in terms of solution properties and equilibria, the complex may also be capable of existing in the solid state. This would be detected via modified substrate solid state properties. The experimental determination of specific stoichiometry and complexation constants as well as modified physical/chemical properties distinguish a complex species from a solid dispersion or a physical mixture involving simple adsorption.

Stoichiometry

Refractive index is an additive property and as such is useful for determining the stoichiometry of organic complexes by the established method of continuous variation. In this method a plot of the components of a mixture where no complexation occurs has a linear relationship. Where complexation does occur between the two components, the value of the additive property (refractive index) passes through a maximum or minimum at the mole fraction corresponding to the stoichiometry of the complex. A plot of refractive index vs. mole fraction of rioprostil in ethanolic PVP solutions at 20° C. shows a maximum in the curve occurs at the mole fractions corresponding to a 1:2.5 stoichiometry, or one rioprostil molecule per 2.5 PVP monomer subunits. The term "PVP monomer subunit", as used herein, refers to the vinyl pyrrolidone monomer of the formula:

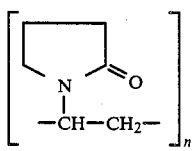

wherein $n = 1$.
(Subunits are more amenable to calculations for a polymer such as PVP having an approximate molecular weight of 40,000.)

Complexation Constant (K)

On the basis of this stoichiometry, the complexation constant (K) was determined in water and in ethanol using the solubility and kinetic methods, respectively, as outlined by Connors and Mollica, J. Pharm. Sci., 1966, 55, 772–780. Excess rioprostil was added to 0, 0.1, 0.5, 1.0, 1.5 and 2.0% aqueous PVP at ambient room temperature and equilibrated over 16.5 hours. UP to a 45% increase in solubility was found with increasing PVP concentration. The data was then plotted as rioprostil molar concentration vs. PVP molar concentration (assign 2.5 PVP subunits as a "mole" of PVP) according to the solubility method of defining complexation parameters. The plot demonstrates a linear relationship ($r^2 = 0.9978$) with a non-zero slope indicating formation of a 1:1 complex. The complexation constant (K) in water was calculated to be $1.43 M^{-1}$.

Likewise, kinetic data obtained showed enhanced rioprostil stability in ethanol when combined with PVP. Here, 100 µg/ml of rioprostil was combined with 0, 0.133, 0.271, 0.537 and 1.44% PVP in ethanol at 50° C. and 60° C. over 11 days. A fourfold improvement in stability was obtained with 0.5% PVP. Data up to 0.5% PVP were plotted according to the kinetic method of determining complexation parameters as $$\frac{k_s}{k_s - k'} \text{ vs. } \frac{1}{[PVP]}$$

where $k_s$ is the rate constant for uncomplexed rioprostil, $k'$ is the observed rioprostil rate constant (both uncomplexed and complexed), and [PVP] is the molar PVP concentration (assign 2.5 PVP subunits as a "mole" of PVP). The plot demonstrates a linear relationship ($r^2 = 0.9807$) with a non-zero slope indicating formation of a 1:1 complex. The complexation constant (K) in ethanol was calculated to be $442 M^{-1}$.

Defined stoichiometry, linearity, and equilibrium constants demonstrate that the rioprostil/PVP matrix exists as a unique chemical entity in solution. When the soluble complex solution is reduced to its solids content by solvent removal, the resultant powder material displays vastly improved thermal stability properties compared to uncomplexed rioprostil: approximately 5% rioprostil complexed to PVP is 40 times more stable than rioprostil alone at 80° C. over 22 days. Supporting solid state data showing differences in rioprostil physical/chemical properties for solid complex vs. uncomplexed neat rioprostil using standard techniques such as DSC, X-ray powder diffraction and melting point, were not applicable due to the oily nature of the drug substance. The following are illustrative actual examples of rioprostil/PVP complex formation.

EXAMPLE 1

Rioprostil/PVP Product Formed by Lyophilization

Stir 1 gram of rioprostil and 20 grams of polyvinylpyrrolidone (PVP) in 1.2 liters of water at ambient temperature overnight until dissolved. Divide the solution into four equal portions in lyophilization flasks and quick freeze each in a dry ice/acetone bath. Lyophilize under about 300 millitorr pressure at a condenser temperature of approximately −60° C. The resultant rioprostil/PVP product was obtained in the form of a white, fluffy solid, weighing 19.3 grams, which was 91.8% of the theoretical yield.

Assay by HPLC indicated that there was 4.65% w/w rioprostil present in the complex, the balance of the solid material being PVP.

EXAMPLE 2

Rioprostil/PVP Product Formed by Evaporation

Stir 1.5 grams of rioprostil and 28.5 grams of polyvinylpyrrolidone (PVP) in 200 ml of absolute alcohol at ambient temperatures until dissolved. Pour the solution into a polyethylene tray and evaporate the ethanol in a vacuum oven at ambient temperature under 28 in Hg for about 48 hours. Introduction of a nitrogen stream into the vacuum chamber helps to facilitate evaporation. Film formation on the surface of the sample may have to be broken intermittently. Remove the resultant yellow to white amorphous dry solid material from the trays and size through a 40 mesh and then a 80–100 mesh screen.

Assay by HPLC indicated that there was 3.76% w/w rioprostil present in the complex, the balance of the material being PVP.

EXAMPLE 3

Rioprostil/PVP Product Formed by Spray Drying

Mix 5.74 grams of rioprostil with 110 grams of polyvinylpyrrolidone (PVP) in methylene chloride at ambient temperature until dissolved to make 900 ml of solution. Spray dry the mixture using a commercially available system such as the Bowen Closed Cycle "BLSA" Laboratory Spray Dryer. A feed rate of 300 mls/min through a two-fluid nozzle with nitrogen as the atomizing medium (50 PSIG) was utilized. Inlet and outlet temperatures of 150° C. and 100° C., respectively, were maintained using indirect steam at 150 PSIG. The product was collected in a Cyclone Collector and obtained as a white-fluffy material. In this manner approximately 78% of the total solid content was recovered, of which 5.21% was identified as rioprostil.

Subsequent experimentation demonstrated comparable results when absolute ethanol is substituted for methylene chloride in the above procedure.

The rioprostil/PVP product of Examples 1–3 can be formed into tablets for oral administration as follows: [Tablets were actually made from the products of Examples 2 and 3 and could be made from the product of Example 1 by following the same procedure].

Independently utilizing the product from Examples 2 and 3, separate batches of 50 and 300 microgram tablets were manufactured.

The formula used for the 50 microgram tablets was:

|  | mg/tab |
|---|---|
| Rioprostil/PVP complex | 1.14 |
| Avicel PH 101 microcrystalline cellulose | 25.0 |
| Lactose DT (anhydrous) | 67.86 |
| Polyplasdone XL (cross-linked PVP) | 3.00 |
| Lubritab-hydrogenated vegetable oil (lubricating agent) | 3.00 |
| | 100.0 mg |

The formula used for the 300 microgram tablets was:

|  | mg/tab |
|---|---|
| Rioprostil/PVP complex | 6.85 |
| Avicel PH 101 | 25.0 |
| Lactose DT (anhydrous) | 62.2 |
| Polyplasdone XL | 3.00 |
| Lubritab | 3.00 |
| | 100.0 mg |

The manufacturing procedure used was:
Screen all ingredients (excluding Lubritab) through a 20 mesh screen. Place in an Engelsman mixer and blend for 10 minutes at 60 rpm. Screen the Lubritab through a 60 mesh screen and add to the blend. Mix for an additional 3 minutes. Compress on a Manesty F-3 single punch tablet press using ¼" flat-faced beveled edge tooling. Tablet fill weight was 100 mg and hardness was 3–8 kg. Tablets collected and initially stored in amber glass bottle with desiccants. Entire procedure performed under controlled (less than 30% RH) humidity conditions due to the stability of the complex.

The tablets so obtained were packaged as Blister packages using an Ivers-Lee uni-strip packer. The package consists of poly/cello/foil, and was successfully tested as follows:

Leak test of blisters during and after packaging. Initial assay and stability of tablets at 50°, 37° and 24° (50% RH) was determined after 30, 90 and 180 days. In addition, disintegration, hardness and color testing were performed. Tablets stored at 5° C. were used as controls. The tablets so tested were satisfactory for use.

The above rioprostil/PVP complex tablets are especially useful as the oral dosage form for inducing cytoprotection, preventing gastrointestinal lesions, and treating gastrointestinal lesions in mammals as taught in U.S. Pat. No. 4,370,348.

If desired, the rioprostil/PVP complexes of the present invention can be utilized not in tablets but in powder form or in capsules or any other pharmaceutically acceptable oral dosage form.

What is claimed is:

1. A rioprostil: non-crosslinked polyvinylpyrrolidone complex of 1 mole fraction of rioprostil per 2½ mole fraction of polyvinylpyrrolidone monomeric subunits in dry solid form.

2. The complex of claim 1 in powdered form.

3. A pharmaceutical composition for oral administration to mammals to induce cytoprotection or prevent gastrointestinal lesions or treat gastrointestinal lesions comprising, as the active ingredient, the rioprostil: polyvinylpyrrolidone complex of claim 2 and a pharmaceutically acceptable carrier.

4. The pharmaceutical composition of claim 3 in the form of a tablet.

5. The pharmaceutical composition of claim 3 in the form of a capsule.

* * * * *